United States Patent [19]
Barnes

[11] Patent Number: 5,871,929
[45] Date of Patent: Feb. 16, 1999

[54] SUPPRESSION OF PYROPHOSPHOROLYSIS IN DNA SEQUENCING AND IN OTHER APPLICATIONS INVOLVING DNA REPLICATION

[76] Inventor: Wayne M. Barnes, 223 Renaldo Dr., Chesterfield, Mo. 63017

[21] Appl. No.: 899,465

[22] Filed: Jul. 23, 1997

Related U.S. Application Data

[60] Provisional application No. 60/022,316 Jul. 23, 1996.
[51] Int. Cl.⁶ .............................. C12Q 1/68; G01N 33/48
[52] U.S. Cl. .................... 435/6; 436/94; 935/77; 935/78
[58] Field of Search ................. 435/6, 91.2; 935/77, 935/78; 436/94

[56] References Cited

U.S. PATENT DOCUMENTS

| | | | |
|---|---|---|---|
| 4,683,195 | 7/1987 | Mullis | 435/91.2 |
| 4,962,020 | 10/1990 | Tabor et al. | 435/6 |
| 5,436,149 | 7/1995 | Barnes | 435/194 |

OTHER PUBLICATIONS

Sanger et al., PNAS 74:5363–5467 (1977).
Hong, Biosci. Rep. 2:907–912 (1982).
McGraw, Anal. Biochem. 143:298–303 (1984).
Tabor and Richardson, PNAS 84:4767–4771 (1987).
Tabor and Richardson, PNAS 86:4076–4080 (1989).
Tabor and Richardson, J. Biol. Chem. 265:8322–8328 (1990).
Akhmetzjanov and Vakhitov, Nucl. Acids Res. 20:5839 (1992).
Caldwell and Joyce, PCR Methods and Applications, 2:28–33 (1992).
Tabor and Richardson, PNAS 92:6339–6343 (1995).
Baskaran et al., Genome Res. 6:633–638 (1996).
Chen and Kwok, Nucl. Acids Res. 25:347–353 (1997).
Lawyer et al., J. Biol. Chem. 264:6427–6437 (1989).

*Primary Examiner*—Lisa B. Arthur
*Attorney, Agent, or Firm*—Senniger, Powers, Leavitt & Roedel

[57] ABSTRACT

A method of inhibiting pyrophosphorolysis during DNA chain length elongation is provided. The method comprises including both $Mn^{++}$ and $Mg^{++}$ in chain-extension and chain-termination reaction mixtures such as those used in DNA sequencing. This method is useful in stabilizing dideoxy-ribonucleoside triphosphate-terminated DNA chains and improving the quality of DNA sequence data obtained via the use of DNA polymerases that do not discriminate against the incorporation of dideoxyribonucleoside triphosphates and other chain terminating agents. Also provided are a reaction mixture and kit for DNA sequencing employing this method.

24 Claims, 2 Drawing Sheets

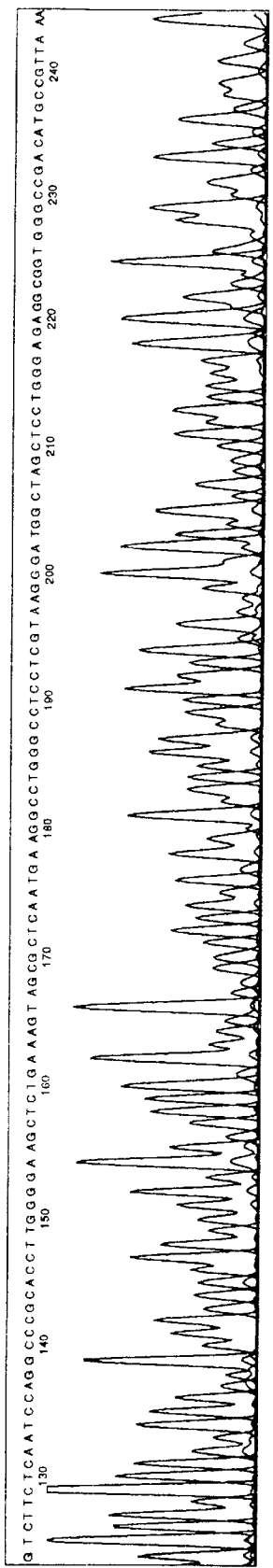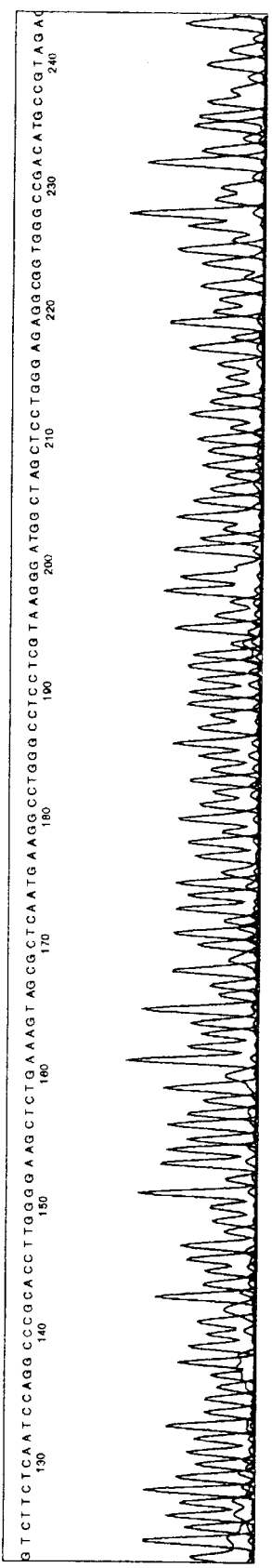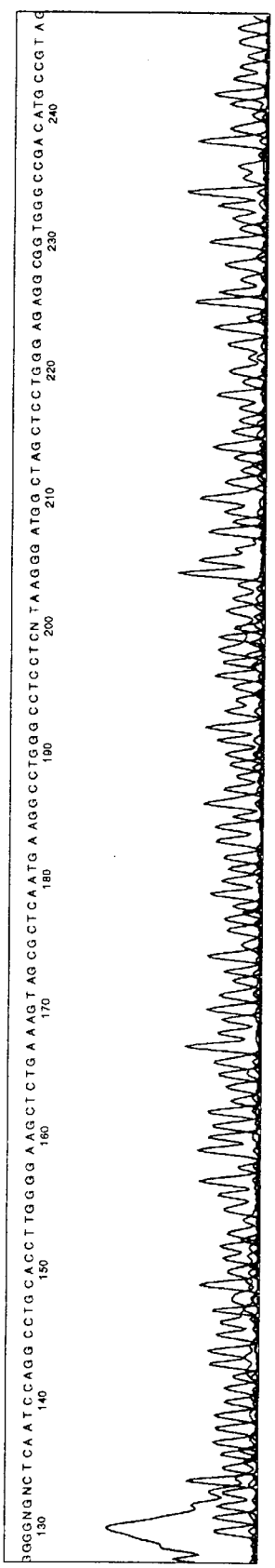

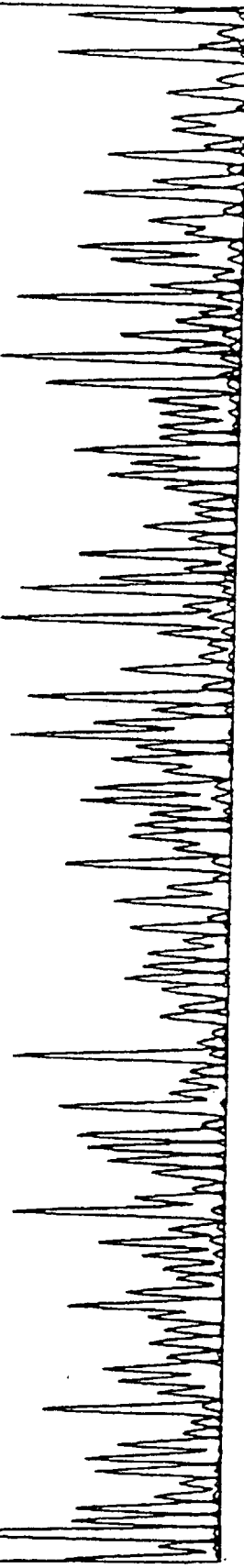
FIG. 2A TAQUENASE AND LOWER (AVE. 1/100) LEVELS OF DYE-ddNTPS;
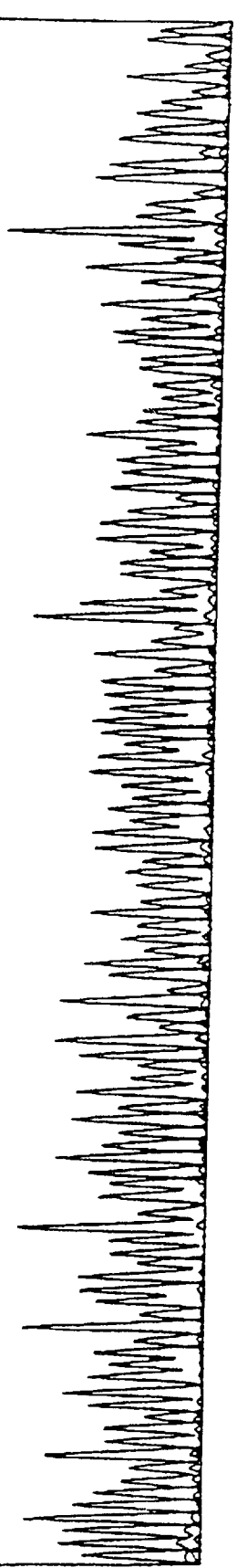
FIG. 2B SAME, BUT WITH MMMM ++;

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear (  i i  ) MOLECULE TYPE: DNA (genomic)

(  i i i  ) HYPOTHETICAL: NO (  i v  ) ANTI-SENSE: NO (  v  ) FRAGMENT TYPE: N-terminal (  v i  ) ORIGINAL SOURCE:
    ( A ) ORGANISM: Thermus aquaticus
    ( B ) STRAIN: YTI (  v i i  ) IMMEDIATE SOURCE:
    ( A ) LIBRARY: synthetic
    ( B ) CLONE: Taq2272'

(  x i  ) SEQUENCE DESCRIPTION: SEQ ID NO:1:

CGGCGGTGCC CTGGACGGGC ATGTT 25

( 2 ) INFORMATION FOR SEQ ID NO:2:

(  i  ) SEQUENCE CHARACTERISTICS:
    ( A ) LENGTH: 29 base pairs
    ( B ) TYPE: nucleic acid
    ( C ) STRANDEDNESS: single
    ( D ) TOPOLOGY: linear (  i i  ) MOLECULE TYPE: DNA (genomic)

(  i i i  ) HYPOTHETICAL: NO (  i v  ) ANTI-SENSE: YES (  v  ) FRAGMENT TYPE: C-terminal (  v i  ) ORIGINAL SOURCE:
    ( A ) ORGANISM: Thermus aquaticus
    ( B ) STRAIN: YTI (  v i i  ) IMMEDIATE SOURCE:
    ( A ) LIBRARY: synthetic
    ( B ) CLONE: KT85

(  x i  ) SEQUENCE DESCRIPTION: SEQ ID NO:2:

GCAGTACCGG GAGCTCACCA AGCTGAAGA 29

( 2 ) INFORMATION FOR SEQ ID NO:3:

(  i  ) SEQUENCE CHARACTERISTICS:
    ( A ) LENGTH: 35 base pairs
    ( B ) TYPE: nucleic acid
    ( C ) STRANDEDNESS: single
    ( D ) TOPOLOGY: linear (  i i  ) MOLECULE TYPE: DNA (genomic)

(  i i i  ) HYPOTHETICAL: NO (  i v  ) ANTI-SENSE: YES (  v  ) FRAGMENT TYPE: C-terminal (  v i  ) ORIGINAL SOURCE:
    ( A ) ORGANISM: Thermus aquaticus
    ( B ) STRAIN: YT1

(  v i i  ) IMMEDIATE SOURCE:
    ( A ) LIBRARY: synthetic
    ( B ) CLONE: Klentaq32

(  x i  ) SEQUENCE DESCRIPTION: SEQ ID NO:3:

GCGAAGCTTA CTACTCCTTG GCGGAGAGCC AGTCC 35

SUPPRESSION OF PYROPHOSPHOROLYSIS IN DNA SEQUENCING AND IN OTHER APPLICATIONS INVOLVING DNA REPLICATION

This application claims benefit under 35 U.S.C. 119(e) of U.S. provisional application 60/022,316, filed Jul. 23, 1996.

Background of the Invention

The present invention relates to DNA replication and to controlled termination of DNA replication. The invention relates, more particularly, to reducing pyrophosphorolysis of the 3'-end of a DNA-reaction product such as the DNA fragments produced during DNA sequencing.

DNA sequencing—the determination of the order in which nucleotides are arranged in a DNA polymer—is typically performed using either chemical hydrolysis or enzymatic replication techniques. DNA sequencing methods based on enzymatic replication require hybridization, chain-extension and chain-termination reactions. Typically, a DNA primer is hybridized to a single-stranded DNA template. The primer is then extended by incorporating non-terminating deoxyribonucleotides that are complementary to the corresponding template nucleotides. The primer-extension reaction continues until a chain-terminating nucleotide or non-nucleotide terminating agent is incorporated into the DNA-product. Both the chain-extension and chain-terminating reactions are catalyzed by a DNA polymerase in the presence of magnesium ion ($Mg^{++}$), and both typically release inorganic pyrophosphatase (PPi) as a by-product of the reaction. The resulting DNA-product fragments each have a common 5'-origin, but are of various sizes—consisting of varying numbers of nucleotides. The DNA-product fragments are separated according to size by high-resolution denaturing gel electrophoresis, and this data is used to infer the order in which the nucleotide bases are arranged within the template (target) DNA.

A number of sequencing formats incorporate the basic enzymatic replication methods. See: Sanger et al. (1977), *Proc. Natl. Acad. Sci. USA*, 74:5463–5467; Tabor and Richardson (1987), *Proc. Natl. Acad. Sci. USA*, 84:4767–4771; Hong (1982) *Bioscience Reports*, 2:907; and McGraw (1984) *Anal. Biochem.*, 143:298. However, these formats may differ in terms of labeling schemes (e.g. label type and position), the number of reactions required (e.g. four independent reactions or a single simultaneous reaction), the relative concentrations of deoxyribonucleoside triphosphates (dNTP's) and chain-terminating reagents (e.g. dideoxyribonucleoside triphosphates—ddNTP's), the type of DNA polymerase (e.g. thermophilic polymerases allowing for cycling approaches, polymerases lacking particular activities, etc.), the strandedness of the template DNA in the initial reaction mixture (e.g. single or double stranded) etc.

Regardless of the particular DNA sequencing format employed, it is of fundamental importance that both the fixed 5'-end and the variable 3'-end be stable for reliable detection. If either the 5'-end or the 3'-end of the DNA-product fragments are altered—for example, by deletion of nucleotides and, for the 3'-end, further extension and termination at a new position—then the quality and reproducability of the DNA sequencing data is markedly reduced. The stability of the 5'-end and/or the 3'-end of the resulting DNA-product fragment can be enhanced by the use of naturally occurring or mutant DNA polymerases which lack 5'-exonuclease activity and/or 3'-exonuclease activity, respectively. However, the 3'-end may still subject to pyrophosphorolytic degradation in the presence of a DNA polymerase having an inherent pyrophosphorolytic activity.

Pyrophosphorolysis relates to the degradation of a 3'-terminal nucleotide (e.g. deoxyribonucleotide or dideoxyribonucleotide) or non-nucleotide 3'-terminal moieties in the presence of inorganic pyrophosphate (PPi). The pyrophosphorolysis reaction is considered to be a reverse reaction of DNA polymerase-catalyzed chain-extension reactions. The reaction products resulting from the degradation depend on the particular moiety present at the 3'-end of the DNA polymer. For example, the degradation products of a DNA fragment having a 3'-dideoxynucleotide includes a corresponding dideoxynucleoside triphosphate and a DNA polymer which has been shortened by one nucleotide at its 3'-end, as represented by the reaction:

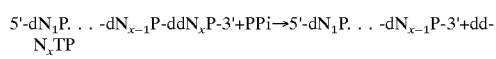

where x is the number of nucleotides in the terminated DNA polymer, dNP is an incorporated nucleotide, ddNP is a 3'-terminal nucleotide, ddNTP represents a dideoxynucleoside triphosphate, and N represents one of the four bases adenine (A), cytosine (C), guanine (G), (T) thymine or analogs thereof.

Hence, pyrophosphorolysis is a bane to accurate and reproducible sequence determination. For example, in dideoxy DNA sequence analysis, the removal of a ddNP at sequence-position "x" by this process is likely to be followed by the incorporation of the non-terminating dNP at "x", thereby leading to a decrease in the amount of DNA-reaction products terminated at "x". Moreover, the extent of pyrophosphorolytic degradation of DNA at a particular sequence-position appears to be sequence-content dependent, so that the data "bands" or "peaks" corresponding to the amount of some DNA-product fragments are relatively diminished or even absent at detectable levels, whereas the bands corresponding to the amounts of other DNA-product fragments are relatively unaffected. (Tabor et al. (1987) *Proc. Natl. Acad. Sci. USA* 84:4767–4771; Tabor et al. (1989) *Proc. Natl. Acad. Sci. USA* 86:4076–4080; Tabor et al. (1990) *J. Biol. Chem.* 265:8322–8328). Decreasing the yield of chain-terminated signals at random sequence-positions is detrimental to the quality of DNA sequence data.

Prior art approaches for reducing the impact of pyrophosphorolysis on enzymatic DNA sequencing protocols includes the addition of pyrophosphatase (PPase) to the reaction mixture in which the DNA-product fragments are formed. See Tabor and Richardson (1990) *J. Biol. Chem.* 265:8322–8328. The inclusion of pyrophosphatase is believed to degrade PPi to inhibit pyrophosphorolysis. However, the inclusion of pyrophosphatase leads to other detrimental effects on the quality of the sequencing results—a decrease in the detected amount of terminated DNA-product fragments which appears to be uniform across sequence positions; the explanation for this negative effect of Ppase is unknown, and it may not occur in all reaction buffer conditions or with all enzymes of this type.

While DNA sequencing is a significant application involving DNA chain extension and termination reactions, other applications involving such reactions also exist. For example, known point mutations in genes can be assayed by methods involving specific primer extension/termination reactions. See Chen and Kwok (1997), *Nucleic Acids Research*, 25:347–353. Because the products of these reactions may be adversely affected by pyrophosphorolytic degradation, the integrity of the involved methods may be jeopardized.

SUMMARY OF THE INVENTION

It is therefore an object of the present invention to improve the quality, reliability and reproducability of enzymatic DNA-sequencing protocols and of other applications involving chain-extension and chain-terminating reactions. It is also an object of the invention to achieve such improved DNA-sequencing results without substantially impacting the present protocols and apparatus used to perform such sequencing.

Briefly, therefore, the present invention is directed to a method for stabilizing a DNA polymer prepared by (i) hybridizing a nucleic acid primer to a nucleic acid template and (ii) reacting the hybridized primer with a deoxyribonucleoside triphosphate or with a chain-terminating agent in the presence of a DNA polymerase. The hybridized primer is reacted with the deoxyribonucleoside triphosphate and/or with the chain-terminating agent in the presence of $Mg^{++}$ and $Mn^{++}$.

The invention is likewise directed to a method for terminating a DNA-extension reaction in which a nucleic acid primer hybridized to a nucleic acid template reacts with a deoxyribonucleoside triphosphate in the presence of a DNA polymerase to form an elongated-DNA polymer. The elongated-DNA polymer reacts with the chain-terminating agent in the presence of $Mg^{++}$ and $Mn^{++}$.

The invention is directed, moreover, to an improvement in a method for determining the nucleic acid sequence of a target DNA polymer. In this method, a DNA primer hybridizes with the target DNA polymer, the hybridized primer reacts with deoxyribonucleoside triphosphates in the presence of a DNA polymerase in a chain-extension reaction to form elongated-DNA polymers, molecules of the elongated-DNA polymers react with some frequency with a chain-terminating agent in a chain-terminating reaction to form a set of DNA-product fragments having various lengths and having a 3' end terminated by the incorporated chain-terminating agent, the DNA-product fragments are separated according to size, and the nucleic acid sequence of the target DNA polymer is inferred from the relative positions of the separated DNA-product fragments. The improvement includes (a) reacting the hybridized primer with the deoxyribonucleoside triphosphates, and/or (b) reacting the elongated-DNA polymer with the chain-terminating agent wherein either and/or both of such reactions are performed in the presence of $Mg^{++}$ and $Mn^{++}$.

The invention is also directed to a method for inhibiting pyrophosphorolysis during chain-termination DNA sequencing, where such sequencing is performed in a sequencing reaction mixture which contains a nucleic acid primer, a nucleic acid template, deoxyribonucleotide triphosphates, a chain terminating agent, a DNA polymerase and $Mg^{++}$. $Mn^{++}$ is added to the sequencing reaction mixture in a concentration effective to inhibit pyrophosphorolysis.

For each of the aforementioned methods, the DNA polymerase is preferably a pol-I type DNA polymerase. The DNA polymerase also preferably has polymerase activity toward dideoxyribonucleoside triphosphates which is at least about equal to its polymerase activity toward deoxyribonucleoside triphosphates. The DNA polymerase is, moreover, preferably a thermostable DNA polymerase. A most preferred DNA polymerase is Klentaq-278, F667Y.

For each of the aforementioned DNA sequencing methods, the target DNA polymer being sequenced consists of a number of nucleotides, n, and each DNA-product fragment consists of a number of nucleotides, m, where m ranges from 1 to n. The standard deviation in the amount of DNA-product fragment having a particular m value—as determined by comparison to the median amount of the DNA-product fragments having m values ranging from 1 to n—is less than the corresponding standard deviation where the target DNA polymer were sequenced in the presence of $Mg^{++}$ but in the absence of $Mn^{++}$, with all other sequencing conditions being equivalent.

Another aspect of the invention is directed to a kit which provides reagents suitable for use in connection with the replication or sequencing of a DNA polymer. The kit includes a container comprising a DNA polymerase, and additionally, one or more of the following: (i) $Mn^{++}$; (ii) a compound containing manganese and capable of forming $Mn^{++}$ in an aqueous solution; and (iii) instructions recommending that DNA replication or sequencing protocols employing the DNA polymerase be performed in a reaction mixture comprising both $Mg^{++}$ and $Mn^{++}$.

According to another embodiment, the kit can include a reagent mixture which comprises one or more deoxyribonucleoside triphosphates, a chain-terminating agent, $Mg^{++}$ and instructions to add $Mn^{++}$ to the reagent mixture at a time which is less than about 1 hour prior to the use of the reagent mixture in DNA sequencing reactions.

The present invention offers improved accuracy and reliability in DNA-sequencing and other applications, such as single-point mutation detection, as compared to prior art methods. Moreover, because such improvements are accomplished using readily-available reagents, they are obtained without substantial impact on the cost involved in performing DNA-sequencing.

Other features and objects of the present invention will be in part apparent to those skilled in the art and in part pointed out hereinafter.

BRIEG DESCRIPTION OF THE DRAWINGS

The above and other objects, features, and advantages of the present invention will be better understood from the following detailed description taken in conjunction with the accompanying drawings, all of which are given by way of illustration only, and are not limiting of the present invention.

FIGS. 1A through 1C show the results of automated DNA sequencing performed in a reaction mixture which includes a 2000 kb template DNA, an appropriate 25 bp primer DNA, Klentaq278-FY DNA polymerase, dNTP's (dATP, dCTP, dTTP, dITP—an analog of dGTP), independently labeled ddNTP's (ddATP, ddCTP, ddTTP and ddGTP), and magnesium ion ($Mg^{++}$) in combination with either water (FIG. 1A) as a control, with manganese ion ($Mn^{++}$) (FIG. 1B) or with pyrophosphatase (PPase) (FIG. 1C) as another control.

FIGS. 2A and 2B show the results of automated DNA sequencing performed in a reaction mixture which includes a 2000 kb template DNA, an appropriate 25 bp primer DNA, TAQUENASE™ DNA polymerase, dNTP's (dATP, dCTP, dTTP, dITP—an analog of dGTP), independently labeled ddNTP's (ddATP, ddCTP, ddTTP and ddGTP), and magnesium ion ($Mg^{++}$) in combination with either water (FIG. 2A) as a control, or with manganese ion ($Mn^{++}$) (FIG. 2B).

DETAILED DESCRIPTION OF THE INNENTION

The following detailed description is provided to aid those skilled in the art in practicing the present invention. Even so, this detailed description should not be construed to unduly limit the present invention as modifications and variations in the embodiments discussed herein can be made by those of ordinary skill in the art without departing from the spirit or scope of the present inventive discovery. The contents of each of the references cited herein are herein incorporated by reference in their entirety.

As used herein, the following abbreviations are intended to have the meanings set forth:

bp=base pairs or number of nucleotides in a single stranded DNA polymer;

kb=kilobase—1000 base pairs; nt=nucleotides;

BME=β-mercaptoethanol, dNP=a nucleotide incorporated into a DNA polymer—typically a deoxyribonucleotide selected from the group consisting of dAP, dCP, dTP, dGP and analogs thereof;

dNTP=deoxyribonucleoside triphosphate—typically selected from the group consisting of dATP, dCTP, dTTP, dGTP and analogs thereof;

ddNP=a chain terminating nucleotide incorporated into a DNA polymer—typically a deoxyribonucleotide selected from the group consisting of ddAP, ddCP, ddTP, ddGP and analogs thereof;

ddNTP=dideoxyribonucleoside triphosphate—typically selected from the group consisting of ddATP, ddCTP, ddTTP, ddGTP and analogs thereof;

$PP_i$=inorganic pyrophosphate;

PPase=pyrophosphatase;

Taq=*Thermus aquaticus* DNA polymerase;

Tfl=*Thermus flavus* DNA polymerase;

Klentaq-nnn=N-terminally deleted *Thermus aquaticus* DNA polymerase that starts with codon nnn+1, although that start codon and the next codon may not match the WT sequence because of alterations to the DNA sequence to produce a convenient restriction site;

WT=wild-type (full length in most prevalent natural form or deletion of only 3 amino acids);

aa=amino acid(s);

ST=Stoffel fragment—an N-terminal deletion of *Thermus aquaticus* DNA polymerase that could be named Klentaq-288;

PCR=as a noun—the polymerase chain reaction or an experiment employing the same, and as a verb—to amplify via the polymerase chain reaction;

According to the present invention, manganese ions ($Mn^{++}$) are included in addition to magnesium ions in standard DNA replication reaction mixtures such as those typically employed in enzymatic DNA sequencing protocols. Without being bound by theory, the inclusion of manganese ions is believed to inhibit pyrophosphorolysis, thereby stabilizing DNA-replication products such as the terminated DNA-product fragments produced during enzymatic DNA sequencing. When the method is used for DNA primer-extension protocols and chain-terminating reactions, such as those involved in sequencing applications, the quality of DNA sequence data is substantially improved. As such, the inclusion of manganese ions in the sequencing reactions can be used to replace and/or to supplement pyrophosphatase presently employed for this purpose.

Chain-extension and chain-termination reactions require, as a substrate, a nucleic acid primer hybridized or annealed to a nucleic acid template. The hybridized/annealed primer is then reacted with chain-extending or chain-terminating reagents in the presence of a template-directed enzyme, $Mg^{++}$ and $Mn^{++}$.

The $Mn^{++}$ can be supplied to the reaction mixture as free ion or as a compound which contains manganese and which is capable of forming $Mn^{++}$ in an aqueous solution. Regardless of how it is supplied, the concentration of $Mn^{++}$ in the final reaction zone for the chain-extension and/or chain-termination reaction, should be an amount sufficient to inhibit pyrophosphorolysis and to thereby stabilize the DNA polymer product or DNA-product fragment formed by such reactions. For DNA sequencing applications in which the target DNA polymer consists of a number of nucleotides, n, and each DNA-product fragment formed consists of a number of nucleotides, m, where m ranges from 1 to n, the pyrophosphorolysis is preferably sufficient inhibited such that the standard deviation in the amount of DNA-product fragment having a particular m value from the median amount of the DNA-product fragments having m values ranging from 1 to n is less than the corresponding standard deviation if the target DNA polymer had been sequenced in the presence of $Mg^{++}$ but in the absence of $Mn^{++}$. That is, when viewing the data resulting from typical DNA sequencing protocols, the peaks corresponding to particular DNA-product fragments appear to be more "even" (less deviation from a mean value) for sequencing performed in reaction mixtures containing both $Mg^{++}$ and $Mn^{++}$ as compared to the results for sequencing with only $Mg^{++}$, but without $Mn^{++}$. The concentration of $Mn^{++}$ present in the chain-extending and/or chain-terminating reaction mixture preferably ranges from about 100 μM to about 3 mM, and, in increasing order of preference, from about 0.5 mM to about 2 mM, from about 0.625 mM to about 1.25 mM, from about 0.75 mM to about 1.5 mM, and from about 0.9 mM to about 1.1 mM. A most preferred concentration of $Mn^{++}$ present in the reaction mixture is about 1.0 mM.

In DNA sequencing applications, the $Mn^{++}$ is preferably added to the reaction mixture shortly before the sequencing reactions (i.e., the chain-extension and chain-termination reactions) are performed. Preferably, $Mn^{++}$ is added to the reaction mixture less than about two hours before the sequencing reactions commence, more preferably less than about 1 hour before, even more preferably less than about 30 minutes before and most preferably less than about 10 minutes before such reactions commence. As such, while other components to be included in a chain-extension and/or chain-termination reaction mixture (e.g. nucleic acid primer and template, chain extenders and/or terminators, template-directed enzymes and $Mg^{++}$) can be preformulated and stored in a refrigerator or freezer for convenience, the $Mn^{++}$ is preferably not included in such a preformulated mixture.

The nucleic acid primer used in the chain-extension and/or chain-termination reactions is a nucleic acid polymer which is substantially complementary to a region of the nucleic acid template. While exact pairing between each nucleotide on the primer and each nucleotide on the template is generally preferred, it is not absolutely necessary. The nucleotides of the primer and template should be sufficiently paired to allow for subsequent chain extension and termination reactions to occur under the particular reaction conditions being employed. Preferably, the primer and template should have less than about 10% unpaired nucleotides, and most preferably less than about 5% unpaired nucleotides. For the preparation of a DNA polymer or for DNA sequencing, the nucleic acid primer is preferably a deoxyribonucleic acid primer (DNA primer). However, for other applications, the primer could be a ribonucleic acid primer (RNA primer) or a molecule which is mostly DNA but has some artificial analogs, such as a dye-label at the 5'-end or thiolation at the 3'-end. The length of the nucleic acid primer is not narrowly critical, and can typically range from about 17 to about 33 nucleotides. The primer is typically a single stranded nucleic acid. However, the primer could be supplied to the reaction mixture as a double-stranded primer, provided that the reaction conditions are controlled to allow for denaturation to form a single-stranded primer. Selection of a particular primer for a particular application is within the skill in the art.

The nucleic acid template is a nucleic acid polymer which is complementary to the DNA polymer/DNA-product fragments being formed. The nucleic acid template is typically a deoxyribonucleic acid template (DNA template)—used in conjunction with a DNA polymerase, but could also be a ribonucleic acid template (RNA template)—used with a reverse transcriptase. The nucleic acid template can be supplied to the reaction mixture as a single stranded nucleic acid or as a double-stranded nucleic acid. When supplied in double-stranded form—for example, as a double-stranded target DNA being supplied to a reaction mixture for DNA sequencing—the reaction conditions are controlled to allow for denaturation to form a single-stranded template. As discussed in more detail below, certain enzymes that catalyze the chain-extension and/or termination reactions are compatible with the higher-temperature environments usually required for forming a single-stranded nucleic acid template. The length of the nucleic acid template is not narrowly critical and will vary depending on the type of application to which the chain extension and/or termination reactions are directed and depending upon the capabilities of the particular enzyme catalyzing these reactions. For DNA sequencing, the number of nucleic acid residues in the target DNA polymer which serves as the nucleic acid template can range from 100 to 1000, and even higher, as improved protocols are developed.

Hybridization or annealing of the nucleic acid polymer to the nucleic acid template can be performed using methods which are well known in the art or with methods developed in the future. While recognizing that some of those skilled in the art would distinguish between "annealing" and "hybridizing" with the former involving non-covalent interactions between DNA-DNA strands and the latter involving non-covalent interactions between DNA-RNA strands, and while endeavoring to honor this distinction in the present description, these terms should be considered interchangeable for purposes of the present application such that the use of one term versus the other will not have a limiting effect on the intended meaning. Specifically, when terms such as "hybridizing" or "hybridized primer" are used in the claims, these terms are intended to include both the hybridizing and annealing concepts. The particular hybridizing or annealing approach employed in the present invention is not significant with respect to the present invention. Typically, the hybridizing/annealing reaction occurs in an aqueous reaction mixture comprising the nucleic acid primer and the nucleic acid template in single-stranded form. The reaction mixture is then incubated at a temperatures ranging from about 60°C. to about 70°C. As discussed below, the nucleic acid primer and template can be hybridized/annealed in the same reaction mixture or reaction temperature zone in which the chain-extension and/or chain termination reactions occur. The product resulting from the hybridization reaction, referred to herein as a hybridized primer (or equivalently, an annealed primer), is the substrate for subsequent chain-extension and chain-termination reactions.

Chain-extension reactions involve the reaction of the hybridized/annealed primer with a chain-extending agent to form an elongated DNA polymer. The chain-extending agent is capable of reacting with the hybridized/annealed primer to incorporate at least one deoxyribonucleotide of at least one particular base (typically C, G, A or T) at the 3'-end of the nucleic acid primer. Typical chain-extending agents include deoxyribonucleoside triphosphates (dNTP's) such as dATP, dGTP, dTTP and dCTP or analogs thereof. Deoxyribonucleoside analogs which are suitable for some applications, and may be preferred for particular DNA sequencing applications, include deoxyriboinosine triphosphate (dITP) —with inosine being a guanine analog—and 7-deaza-dGTP. The chain-extending agents may be labeled or unlabeled, depending on the particular application in which they are being used. The chain-extension reaction are typically carried out in an aqueous solution.

The particular chain-extending reagents included in a given reaction mixture will also depend on the application for which the chain-extension reaction is being used. In some applications, it will be desirable to react a hybridized/annealed primer with dNTP's or analogs thereof having only one particular base (e.g. only dCTP's). Depending on the nucleic acid template, this reaction could form an elongated DNA polymer which is only a single nucleotide longer than the nucleic acid primer, or perhaps, several nucleotides longer. For example, a known point-mutation in a gene can be assayed by (i) hybridizing a primer to the region of the suspect gene which is immediately adjacent the suspected mutation, (ii) reacting the hybridized primer with a labeled deoxyribonucleside triophosphate (dNTP*) having a base which is complementary to either the normal or mutant nucleotide at the suspected defect site, and then (iii) determining whether or not the dNTP* was incorporated into the resulting DNA polymer. Such a method would detect the presence or absence of the point mutation provided that dNTP's of other bases are excluded from the reaction mixture. In other applications, it may be desirable to include dNTP's of a selected mixture of bases (e.g. only dCTP's and dATP's). In many applications, such as in typical DNA sequencing protocols, it is preferably to include each of the four type's of dNTP's—dATP, dCTP, dTTP and dGTP—or their analogs in a reaction mixture to allow the chain elongation reaction to continue for the entire length of the single-stranded nucleic acid template or until the extension reaction is terminated (for example, by incorporation of a chain-terminating agent, as discussed below). For some applications (e.g. mutation detection assays), the DNA polymer formed by the chain-extension reactions preferably comprises a number of nucleotides which is less than about 50 nucleotides greater than the number of nucleotides in the nucleic acid primer, and more preferably less than about 20 nucleotides greater than the number of nucleotides in the nucleic acid primer.

Chain-termination reactions typically involve the reaction of hybridized/annealed primer or a hybridized/annealed elongated DNA polymer (formed, for example, by a DNA-extension reaction) with a chain-terminating agent to form a DNA product having a chain-terminating nucleotide incorporated at its 3'-end. The chain-terminating agent is a reagent capable of reacting with a nucleic acid polymer which is hybridized/annealed primer to a nucleic acid template to incorporate at least one nucleotide or other moiety at the 3-end of the polymer, where incorporated nucleotide or other moiety precludes further chain-extension reaction. Typical chain-extending agents include dideoxyribonucleoside triphosphates (ddNTP's) such as ddATP, ddGTP, ddTTP and ddCTP or analogs thereof. Dideoxyribonucleoside analogs which may be suitable for some applications include dideoxyriboinosine triphosphate (ddITP). Non-nucleoside chain-terminating agents—such as acyclovir—may also be employed with the present invention. The chain-extending agents may be labeled or unlabeled, depending on the particular application in which they are being used. Chain-termination reactions are typically carried out in an aqueous solution.

The particular chain-terminating reagents included in a given reaction mixture will, in a manner similar to the inclusion of particular chain-extending reagents, depend on the application for which the chain-termination reaction is being used. In many applications, it will be desirable to react a hybridized/annealed primer or DNA polymer with ddNTP's or analogs thereof having only one particular base (e.g. only ddCTP's). This approach could be used, for example, in DNA sequencing protocols in which four independent reactions are carried out to form sets of DNA-product fragments—with each set corresponding to DNA-product fragments terminated with a nucleotide having the same particular base (e.g. ddCT). This approach could also be used in the point-mutation assay described above in connection with chain-extension applications. In other applications, it may be desirable to include ddNTP's of a selected mixture of bases (e.g. only ddCTP's and ddATP's). In many applications, such as in DNA sequencing protocols using four differently-labeled chain-terminating agents in a single reaction mixture, it is preferably to include each of the four type's of ddNTP's—ddATP, ddCTP, ddTTP and ddGTP—or their analogs in a reaction mixture.

Moreover, chain-extending and chain-terminating agents can be used in combination in a single reaction mixture, as is typically required in DNA sequencing protocols. In such situations, the relative concentration of reagents included in the reaction zone will depend upon the objective of the protocol. Consideration is typically given to the relative concentration of chain extenders versus chain terminators (e.g. [dNTP's] versus [ddNTP's]) as well as to relative concentrations of one type of reagents (e.g. chain extenders) of one base versus another base (e.g. [dATP] versus [dCTP]). Determination of optimal relative concentrations for a particular application is well within the skill in the art.

The chain-extension and chain-termination reactions are catalyzed by template-directed enzymes. Typically a DNA polymerase is used to catalyze extension/termination of a nucleic acid primer hybridized to a DNA template. However, other template-directed enzymes can be employed, as appropriate. For example, a reverse transcriptase can be used when the substrate is a nucleic acid primer hybridized to a RNA template. While the type of DNA polymerase used in conjunction with the present invention is not narrowly critical, the DNA polymerase is preferably a pol I type DNA polymerase. The DNA polymerase can be a thermophilic or thermostable polymerase. As used herein applied to DNA polymerases, "thermostable" refers to the capability of polymerase enzymes of withstanding temperatures up to 95° C. or 98°C. for many minutes without becoming irreversibly denatured, and the capability of catalyzing the polymerization of DNA at relatively high temperatures (60°to 75° C.). The use of such thermostable DNA polymerases allows for cyclic DNA sequencing protocols, and enhances the efficiency, specificity, and yield of the sequence data. DNA polymerase can lack 5'-exonuclease and/or 3'-exonuclease activities. Use of such polymerases helps improve the stability of the resulting DNA polymer product or DNA product fragment. For the present invention, the DNA polymerase should most preferably, moreover, have polymerase activity which does not adversely discriminate against ddNTP's versus dNTP's. That is, the DNA polymerase activity toward dideoxyribonucleoside triphosphates is at least about equal to its polymerase activity toward deoxyribonucleoside triphosphates, thereby improving the yield of DNA-product fragments during DNA sequencing, and decreasing the costs of labelled terminators. The DNA polymerase can be a wild-type polymerase or a mutant polymerase. The DNA polymerase can, independently, be obtained from a natural source or by synthetic preparation, including by recombinant methods. While a number of preferred DNA polymerases are described hereinafter, these should not be considered limiting to the scope of the present invention.

Taq DNA polymerase—DNA polymerase obtained from the hot springs bacterium *Thermus aquaticus*—have been shown to be quite useful in the amplification of DNA, in DNA sequencing, and in related DNA primer extension techniques by virtue of its thermostability. The DNA and amino acid sequences disclosed by Lawyer et al. (1989) *J. Biol. Chem.* 284:6427, GenBank Accession No. J04639, define the gene encoding *Thermus aquaticus* DNA polymerase and the corresponding DNA polymerase enzyme, respectively. The DNA and amino acid sequences of the highly similar DNA polymerase expressed by the closely related bacterium *Thermus flavus* (Tfl DNA polymerase) have been described by Akhmetzjanov et al. (1992) *Nucl. Acids Res.* 20:5839, GenBank Accession No. X66105. These enzymes are representative of a family of DNA polymerases, including *Thermus thermophilus* DNA polymerase, which are thermostable.

DNA polymerases lacking the 5'-exonuclease activity inherent in many DNA polymerases are also known in the art. Typically, the 5'-exonuclease activity is removed by proteolytic or recombinant DNA mutagenesis of the encoding gene. For *E. coli* DNA polymerase I, the resulting product is known as the large fragment or as "Klenow fragment." For Taq DNA polymerase, such useful mutants include those containing an N-terminal deletion of 278 amino acids, or any of several N-terminal deletions in the range of 235 to 292 amino acids (specifically 235, 271, 271, 278, 289, and 292 amino acids), or a point mutation such as D46A. See, for example, U.S. Pat. No. 5,436,149 to Barnes. 5'-exonuclease activity is disadvantageous since it can remove a variable number (such as 0,1, or 2) of nucleotides from the 5' end of the analyzed chains, thus destroying or complicating the DNA sequence pattern. That is, a triplet will often be produced for each single desired band, and the correct sequence cannot be inferred.

Preferred enzymes lacking a 3'-exonuclease activity include DNA polymerases such as *E. coli* DNA polymerase I and phage T7, T3, and T4 DNA polymerases.

DNA polymerases that do not discriminate against the incorporation of chain-terminators (such as dideoxyribonucleotides) into an elongating DNA polymer in the presence of $Mg^{++}$ alone (without $Mn^{++}$) as compared to dNTP's are the most preferred DNA polymerases. These polymerases include, for example, mutant forms of *Thermus aquaticus, Thermus flavus*, and *E. coli* pol I DNA polymerases wherein in the domain responsible for distinguishing between dNTPs and ddNTPs, phenylalanine is replaced with tyrosine. These polymerases exhibit a preference for, i.e., catalyze increased incorporation of, or exhibit decreased Kms for, ddNTPs (dideoxynucleoside triphosphates) as compared to natural dNTP (deoxynucleoside triphosphate) substrates. Exemplary DNA polymerases of this type include mutant forms of *E. coli* and Taq DNA polymerases which contain an F→Y (phenylalanineetyrosine) mutation that reduces or eliminates discrimination against the incorporation of ddNTPs (versus dNTP's) into a DNA-product fragment. See Tabor and Richardson (1995), *Proc. Natl. Acad. Sci. USA* 92:6339–6343. Other DNA polymerases, such as those from bacteria of the genus Mycobacterium, contain the same FY substitution in the their naturally occurring sequence, and could non-discriminatively catalyze the incorporation of ddNTPs relative to dNTPs. Id. at 6343. Approximately 100-fold to 5000-fold lower levels of ddNTPs can reportedly be used during the Sanger sequencing method or its cycled equivalent when a DNA polymerase of this type is employed in such protocols. Another such DNA polymerase is a mutant form of Taq polymerase which combines the phenylalanine to tyrosine substitution at position 667 (F667Y) with an N-terminal deletion of 278 amino acids, referred to as Klentaq278-FY or alternatively, Klentaq-278, F667Y herein. See U.S. Pat. No. 5,436,149 to Barnes. This *Thermus aquaticus* DNA polymerase having an amino acid change F667Y and having a $NH_2$ terminal from which 278 amino acids have been deleted.

Unlike the effect of $Mn^{++}$ (used alone as a substitute for $Mg^{++}$) on DNA polymerases that discriminate against ddNTPs (such as T7 DNA polymerase, Klenow fragment, and Taq polymerase), $Mn^{++}$ (used alone in place of $Mg^{++}$) does not enhance the incorporation of ddNTPs when used with DNA polymerases (such as Klentaq278-FY) which do not discriminate against the incorporation of ddNTP's as compared to dNTP's. See U.S. Pat. No. 4,962,020 to Tabor et al. That is, for this class of non-discriminating DNA polymerases, the use of lower ddNTP/dNTP ratios leads to poor termination efficiency, based on experimental results with Klentaq278-FY in the presence of $Mn^{++}$ alone and in the absence of $Mg^{++}$ (data not shown). Moreover, in the absence of manganese ions, these polymerases produce a markedly uneven presentation of bands or peaks representing chain-terminated molecules and information-bearing sequence data. Some of the peaks are so unevenly present on the low side, i.e., the peaks are so small, that they are effectively missing. The unevenness (large deviation from the mean peak value) of the peaks is caused, to a significant extent, by a local-DNA-context dependent removal of terminal 3'-dideoxynucleotides by recombining them with PPi (inorganic pyrophosphate) due to the inherent pyrophosphorolytic activity of the DNA polymerase. The pyrophosphorolytic activity is sequence context dependent due to factors which are at present unpredictable, but which tend to act with the same relative efficiency on each like molecule in the reaction mixture.

The reaction mixture should contain, in addition to the nucleic acid primer which has been hybridized/annealed to the nucleic acid template, chain-extending and/or chain-terminating reagents and the template-directed enzymes described above, both $Mg^{++}$ and $Mn^{++}$. The amount of $Mg^{++}$ in the reaction mixture can be an amount typically used under existing protocols when $Mg^{++}$ was employed in such reaction mixtures without $Mn^{++}$. For DNA sequencing applications, typical concentrations of $Mg^{++}$ range from about 1.5 mM to about 6 mM. However, concentrations of $Mg^{++}$ outside of this range may also be used as directed by the particular application. The determination of an appropriate concentration of $Mg^{++}$ for particular chain-extension and/or chain-termination reactions is within the skill in the art. Significantly, the $Mn^{++}$ of the present invention is included supplementally to, not as a replacement for, the $Mg^{++}$ typically employed. As noted by previous work in the art, the substitution of $Mn^{++}$ for $Mg^{++}$ does not significantly affect, or at least does not improve, chain-extension and/or chain-termination reactions catalyzed by *E. coli* DNA polymerase I F762Y and Taq DNA polymerase F667Y. See Tabor and Richardson (1995), *Proc. Natl. Acad. Sci. USA* 92:6339–6343 at 6343. In contrast, presently described combination of $Mg^{++}$ and $Mn^{++}$ results in substantially improved DNA sequencing results. See Examples 1 and 2.

The chain-extending and/or chain-terminating reaction mixtures can also contain other components which facilitate their respective reactions. For example, Tris base at pH ranging from about 8.5 to about 9.5 can be included.

Moreover, according to another aspect of the present invention, I have discovered that the results of enzymatic DNA sequencing methods, particularly the temperature-cycling type sequencing protocols, can be improved with respect to quality and reproducability by including betaine during the chain-extension and chain-termination reactions catalyzed by a DNA polymerase. Betaine has the molecular formula $C_5H_{11}NO_2$ and is available from Sigma Chemicals (St. Louis, Mo.) as Cat. No. B-2629. Without being bound by theory, the betaine is believed to relax slightly the tertiary structure of the DNA template in a manner which enhances the chain-extension and chain-termination reactions. Betaine is preferably included in standard chain-extension and/or chain-termination reaction mixtures at a concentration ranging from about 0.7M to about 1.8M, more preferably at a concentration ranging from about 1.0M to about 1.5M, and most preferably at a concentration ranging from about 1.3M to about 1.5M. A concentration of betaine of about 1.3M is most preferred. However, for a given particular application, the preferred optimal concentration could lie outside of the recited ranges. The exact concentration optimum appears to be dependent upon details of reaction volume, geometry and sealing of the reaction vessels, and as such, can be determined using standard experimental protocols known in the art. Importantly, the betaine can be used advantageously in standard reaction mixtures either independently of $Mn^{++}$, or in combination with $Mn^{++}$. Including betaine in DNA sequencing protocols results in data having relatively higher signals of bands that are representative of the amount of DNA-product fragment formed of a particular length.

In a preferred application of the present invention, the nucleic acid sequence of a target DNA polymer is determined. (See, for example, Examples 1 and 2). In a preferred DNA sequencing protocol, a reaction vessel is supplied with a DNA primer and the target DNA polymer template—both in single-stranded form. However, when a temperature-cycling DNA sequencing protocol is employed, a double-stranded primer and/or target DNA polymer can be used effectively. Deoxyribonucleoside triphosphates of each base (dATP, dTTP, dCTP and dGTP or analogs thereof such as dITP), and one or more chain terminators, preferably dideoxyribonucleoside triphosphates of one or more particular bases (ddATP, ddTTP, ddCTP and ddGTP or analogs thereof) are also supplied to the reaction vessel, along with an appropriate amounts of DNA polymerase (e.g. Klentaq-278, F667Y), $Mg^{++}$, $Mn^{++}$ and betaine as described. The $Mn^{++}$ is added just shortly (less than about 10 minutes) before initiating the sequencing reactions.

A wide variety of labeling and sequence reaction schemes can be employed. Typically at least one of the nucleic acid primer, the deoxyribonucleoside triphosphates or the chain-terminating agents are detectably labeled such that, after the sequencing reactions are complete, a given DNA-product fragment is labeled at its 5'-end (e.g. labeled primer), within the elongated DNA polymer (e.g. labeled dNTP such as $\alpha$-$^{32}$PdATP), or at its 3'-end (e.g. labeled ddNTP such as $\alpha$-$^{32}$PddATP). Any suitable label known in the art can be employed, including for example, radioactive labels or fluorescent labels. As fluorescent labels are typically referred to as "dyes", dye-labeled ddNTP's are sometimes referred to in the art as "DYE-ddNTP's" or "DYE-terminators". Other labels are also known in the art. The DNA sequencing reactions are preferably performed in a single reaction using, for example, labeled ddNTP's of each of the four bases with each ddNTP base-type having a different detectable label. Alternatively, the DNA sequencing reactions could be carried out in four independent reactions using for each reaction, for example, a labeled ddNTP of only one base type. Other variations on DNA sequencing schemes are known in the art. The schemes described herein should be considered exemplary and not limiting as to the scope of the present invention.

The sequencing reactions (i.e., chain-extension and chain-termination reactions) are preferably carried out by repetitive cycling of the temperature of the reaction mixture. This approach requires the use of a thermostable DNA polymerase. Briefly, the reaction mixture is heated to a first temperature sufficient to denature double-stranded nucleic acid polymer present in the reaction mixture (e.g. double-stranded DNA primer, double-stranded DNA template and after the first cycle, DNA-product fragments hybridized/annealed to the DNA template)—typically a temperature ranging from about 90°C. to about 98°C. The reaction mixture is subsequently cooled to a second temperature which allows the DNA primer to hybridize/anneal to a DNA template strand (from the target DNA polymer being sequenced)—typically a temperature ranging from about 50°C. to about 68°C. The reaction mixture is then either left at a temperature within this same temperature range, or optionally, heated slightly to a third temperature—typically a temperature ranging from about 65°C. to about 72°C.—at which temperature the reaction mixture is incubated longer, thereby allowing the hybridized primer to react with deoxyribonucleoside triphosphates in a chain-extension reaction to form an elongated-DNA polymer, and to allow the elongated-DNA polymer to react with a chain-terminating agent in a chain-terminating reaction to form a DNA-product fragment. The time spent at the various temperatures of the cycle depends on a number of factors which are known and or can be determined by those skilled in the art. Exemplary times include: at the first, denaturing temperature—times ranging from about 5 seconds to about 15 seconds; at the second, hybridizing temperature—times ranging from about 15 seconds to about 30 seconds; and at the third, incubating temperature—times ranging from about 30 seconds to about 240 seconds. After a complete temperature cycle, subsequent cycles are performed such that the chain-extension and chain-terminating reactions are repeated, with each cycle forming a set of DNA-product fragments having various lengths and having a 3' end terminated by the incorporated chain-terminating agent (dNP).

The DNA-product fragments are separated by methods known in the art. The separation is preferably effected electrophoretically—for example, on polyacrylamide gel. The separated DNA-product fragments can then be analyzed manually or by using automated analyzers known in the art. The nucleic acid sequence of the target DNA polymer is inferred from the relative positions of the separated DNA-product fragments.

In another aspect of the present invention, $Mn^{++}$ is included in a reagent mixture suitable for use in protocols directed to replicating or sequencing a target DNA polymer. An exemplary reagent mixture comprises one or more deoxyribonucleoside triphosphates, a chain-terminating agent, $Mg^{++}$ and instructions to add $Mn^{++}$ to the reagent mixture at a time which is less than about 1 hour prior to the start of the sequencing reactions.

In a further aspect of the present invention, a reagent kit suitable for use in replicating or sequencing a DNA polymer is provided. The kit comprises a first container that includes a template-directed enzyme, and preferably a DNA polymerase. The kit also includes either or both of the following: (a) a second container comprising (i) $Mn^{++}$ or (ii) a compound containing manganese and capable of forming $Mn^{++}$ in an aqueous solution; or (b) instructions recommending that DNA replication or sequencing protocols employing the DNA polymerase be performed in a reaction mixture comprising both $Mg^{++}$ and $Mn^{++}$, and preferably with $Mn^{++}$ at the concentrations described above. The kit may also contain other components useful for DNA sequencing.

The following examples illustrate the principles and advantages of the invention.

EXAMPLES

Example 1

A 2000 kb target DNA polymer was sequenced using the protocols of the present invention. Briefly, stock solutions were prepared as follows: 10× T.C.A.M. (including: 500 mM Tris-HCl—pH 9.2; 160 mM ammonium sulfate; and 35 mM $MgCl_2$); and a DYE-ddNTP mix B consisting essentially of fluorescent terminating agents (including 1.8 $\mu$M DYE-ddCTP, 3.6 $\mu$M DYE-ddTTP, 0.15 $\mu$M DYE-ddATP and 80 nM DYE-ddGTP). These stock solutions were used to prepare a reaction mixture to be used in a thermal-cycling DNA sequencing protocol in which each single 20 $\mu$l cycle involved a sequencing reaction mixture that contained: water to final volume of 20 $\mu$l; 150 $\mu$M of each of dATP, dCTP, and dTTP; 450 $\mu$M dITP; 1 $\mu$l of DYE-ddNTP mix B; 2 $\mu$l of 10× T.C.A.M.; 5 pmoles primer (SEQ ID NO:1); 20 ng target DNA polymer produced by PCR amplification; 4 units Klentaq278-FY DNA polymerase; and 1 $\mu$l of a "test" component which was either: water as a control (FIG. 1A); 20 mM $MnSO_4$ (FIG. 1B); or 0.5 unit thermostable pyrophosphatase (New England Biolabs, Cat. No. 296) (FIG. 1C).

The PCR amplicon being used as the target DNA polymer derives from *Thermus aquaticus* DNA as template (or a clone of its gene encoding DNA polymerase), and primers SEQ ID NO:2 and SEQ ID NO:3. See U.S. Pat. 5,436,149 to Barnes.

The hybridization, chain-extension and chain-termination reactions, DNA-product fragment separation and DNA-sequence analysis were performed as follows. The 20 $\mu$l reaction mixtures were temperature-cycled for 25 cycles of 50 seconds at 96° C., 30 seconds at 64° C., and 3 minutes 65° C. They were then ethanol-precipitated by adding one volume (20 $\mu$l) of 2× BlueAcetate (0.6M sodium acetate, pH 5.4; 2 mg/ml blue dextran (carrier and loading dye)). Then, 3–4 volumes of ethanol (120 $\mu$l) were added. The mixture was chilled, centrifuged hard for 8 minutes or at 3,000 rpm for 30 minutes, and the supernatants were removed. Three drops of 75% salt-free ethanol were then added. Tubes were then centrifuged hard for 4–10 minutes, the supernatants were removed, and the pellets were dried. The samples were prepared for loading by adding 3 $\mu$l pure formamide that had been stored in the dark. The samples were heated for 30 minutes at 90° C., mixed, and loaded (2 $\mu$l) onto a 4% polyacrylamide gel. The samples were analyzed according to the instructions for an automated fluorescent DNA sequence analyzer such as the ABI 373, 310, or 377 (Applied Biosystems, Inc.). The results are shown in FIGS. 1A and 1B (the original data are in color, with a different color for each ddNTP).

As shown in FIG. 1A, the expectation (predicted by Tabor and Richardson, 1995, supra) that the FY mutant Klentaq278 DNA polymerase would create "even" peaks (ie, low standard deviation from a median peak value) in the presence of magnesium ion, $Mg^{++}$, alone was not realized. Moreover, while the results shown in FIG. 1C shows that somewhat more "even" peaks resulted when pyrophosphatase was included with $Mg^{++}$ in the reaction mixture—due to pyrophosphatase degradation of PPi which prevents pyrophosphorolysis by removing one of its substrates, the overall amplitude of these peaks is low as compared to the peaks in the control. The lower peak heights are a typical undesirable side effect of the PPase enzyme. In fact, the results obtained with PPase are typically much worse—that is, the signals are much lower—than the results shown in FIG. 1C.

FIG. 1B shows the results obtained employing the method of the present invention, wherein 1 mM $MnSO_4$ is added to the magnesium-containing reaction mixture. These results are much better than those obtained using pyrophosphatase (cf. FIG. 1C), exhibiting more "even" peak heights (that is, less deviation from the median value of the peaks). Significantly, the small peaks have become average in height, or are less small, than when pyrophosphatase is employed—providing for an improved signal. Higher peaks are somewhat reduced in height, suggesting that $Mn^{++}$ may partially inhibit the incorporation of DYE-dd terminators. To the extent that this is the case, under these conditions, $Mn^{++}$ is having an effect opposite to that disclosed in U.S. Pat. No. 4,962,020 to Tabor and Richardson, where manganese is reported to stimulate the incorporation of chain terminating agents by certain DNA polymerases. The presence of 3 mM sodium isocitrate in the reaction mixture has no significant effect on the sequencing results.

While not intending to be bound to any particular explanation of my invention, the similar results obtained with manganese and pyrophosphatase suggest that these agents act at the same point in the sequencing reaction—to stabilize terminated DNA chains by reducing pyrophosphorolysis.

Example 2

A DNA sequencing protocol similar to that followed in Example 1 was performed, with somewhat improved results as compared to those reported in Example 1. Briefly, each sequencing reaction contained: water to 20 µl final volume (added first); 2 µl 10× T.C.A.M. prepared as in Example 1; 5 pmoles primer (SEQ ID NO:1); 200 ng target DNA polymer (as in Example 1); 4 units (50–80 ng) Klentaq278-FY DNA polymerase; 1 µl of a "CTIA" dNTP mixture comprising dCTP, dTTP, dATP and dITP (as described below); 1 µl of DYE-ddNTP mix (as described below); 1 µl 20 mM $MnSO_4$ (FIG. 2B) or water (FIG. 2A) (for the control—without $Mn^{++}$).

500 µl of CTIA dNTP mixture were prepared by combining water with individual 100 mM dNTP stocks as follows: 15 µl dATP, 37.5 µl dCTP, 37.5 µl dTTP, and 22.5 µl dITP.

DYE-ddNTP mix was prepared in either of two ways, using the darkly colored product available from Perkin-Elmer (Cat. No. 401095): a) all four DYE-ddNTPs diluted 1/100 in water, i.e., 96 µl water plus 1, 1, 1, 1 µl, or b) the darkly colored 2× Prism kit (Applied Biosystems, Inc.) diluted 1/30 with water. For this method, the enzyme, dNTPs, and other components in the 2× Prism kit were ignored. 200 µl of the 2× sequencing kit was prepared by mixing 118 µl water, 40 µl 10× T.C.A.M., 20 µl dNTP mix "CTIA", 20 µl ddNTP/100, and 2 µl Klentaq278-FY. This was stored at 4° C. For use, 10 µl of the 2× sequencing kit was mixed with 9 µl DNA plus 1 µl 20 mM $MnSO_4$.

The hybridization, chain-extension and chain-termination reactions, DNA-product fragment separation and DNA-sequence analysis were performed as follows. The thermal cycling protocol included: 25 cycles of 50" at 97° C. (Only 94° if DMSO is included); 15" at 50°C. (if primer is shorter than 25 bases); and 240" at 65°C. (PTC-ZOO block control, hot top).

The results obtained without manganese ion, $Mn^{++}$ (i.e., with only magnesium, $Mg^{++}$ present in the reaction mixture) are shown in FIG. 2A. While the overall amplitude of the signal is good, the peaks are greatly "uneven" (have a relatively large standard deviation from a median value for the peaks).

The results obtained via the present inventive method, with 1 mM $Mn^{++}$ added to the magnesium-containing reaction mixture, are shown in FIG. 2B. The peak heights are much more even (that is, have a much smaller standard deviation from a median value for the peaks) under these conditions relative to the data in FIG. 2A. Moreover, as observed with regard to the results obtained in Example 1, the striking parallel between the results obtained using pyrophosphatase compared with those obtained using both $Mn^{++}$ and $Mg^{++}$ clearly implies that $Mn^{++}$ acts by inhibiting pyrophosphorolysis.

The invention being thus described, it will be apparent that the same can be varied in many ways. Such variations are not to be regarded as a departure from the spirit and scope of the present invention, and all such equivalents to one skilled in the art are intended to be included within the scope of the following claims.

What is claimed is:

1. A method for stabilizing a DNA polymer prepared by hybridizing a nucleic acid primer to a nucleic acid template and reacting the hybridized primer with a deoxyribonucleoside triphosphate or with a chain-terminating agent in the presence of a DNA polymerase, the method comprising reacting the hybridized primer with the deoxyribonucleoside triphosphate or with the chain-terminating agent in the presence of $Mg^{++}$ and $Mn^{++}$.

2. The method of claim 1 wherein the DNA polymer formed comprises a number of single-stranded nucleotides which is less than about 50 nucleotides greater than the number of nucleotides in the nucleic acid primer.

3. A method for terminating a DNA-extension reaction in which a nucleic acid primer hybridized to a nucleic acid template reacts with a deoxyribonucleoside triphosphate in the presence of a DNA polymerase to form an elongated-DNA polymer, the method comprising reacting the elongated-DNA polymer with a chain-terminating agent in the presence of $Mg^{++}$ and $Mn^{++}$.

4. In a method for determining the nucleic acid sequence of a target DNA polymer wherein a DNA primer hybridizes with the target DNA polymer, the hybridized primer reacts with deoxyribonucleoside triphosphates in the presence of a DNA polymerase in a chain-extension reaction to form elongated-DNA polymers, molecules of the elongated-DNA polymers react with some frequency with a chain-terminating agent in a chain-terminating reaction to form a set of DNA-product fragments having various lengths and having a 3' end terminated by the incorporated chain-terminating agent, the DNA-product fragments are separated according to size, and the nucleic acid sequence of the target DNA polymer is inferred from the relative positions of the separated DNA-product fragments, the improvement comprising reacting, in the presence of $Mg^{++}$ and $Mn^{++}$, (a) the hybridized primer with the deoxyribonucleoside triphosphates, or (b) the elongated-DNA polymer with the chain-terminating agent.

5. The method of claim 4 wherein (a) the hybridized primer is reacted with the deoxyribonucleoside triphosphates, and (b) the elongated-DNA polymer is reacted with the chain-terminating agent, wherein both of the reactions are performed in the presence of $Mg^{++}$ and $Mn^{++}$.

6. The method of claim 4 wherein the target DNA polymer is supplied to the reaction mixture as a single-stranded DNA polymer.

7. The method of claim 4 wherein the DNA polymerase is a pol-I type DNA polymerase.

8. The method of claim 4 wherein the DNA polymerase is a pol-I type DNA polymerase having polymerase activity toward dideoxyribonucleoside triphosphates which is at least about equal to its polymerase activity toward deoxyribonucleoside triphosphates.

9. The method of claim 4 wherein the DNA polymerase is Klentaq-278, F667Y.

10. The method of claim 4 wherein the DNA polymerase is a pol-I type thermostable DNA polymerase.

11. The method of claim 4 wherein the DNA polymerase is a *Thermus aquaticus* DNA polymerase having tyrosine substituted for phenylalanine at amino acid position 667 of the wild-type polymerase sequence.

12. The method of claim 4 wherein the DNA polymerase is a pol-I type Taq DNA polymerase having a $NH_2$-terminal portion from which 235 to 292 amino acids have been deleted.

13. The method of claim 4 wherein the DNA polymerase is selected from the group consisting of *E. coli* DNA polymerase I F762Y, Taq DNA polymerase F667Y, Taq DNA polymerase F667Y having a reduced 5' exonuclease activity, Taq DNA polymerase F667Y having a $NH_2$-terminal portion from which 235 to 292 amino acids have been deleted, and Taq DNA polymerase F667Y having point mutation D46A.

14. The method of claim 4 wherein the chain-terminating agent is one or more dideoxyribonucleoside triphosphates.

15. The method of claim 4 wherein the chain-terminating agent is detectably labeled.

16. The method of claim 4 wherein the deoxyribonucleoside triphosphates are selected from the group consisting of dATP, dGTP, dTTP, dCTP and analogs thereof.

17. The method of claim 4 wherein the target DNA polymer consists of a number of nucleotides, n, wherein each DNA-product fragment consists of a number of nucleotides, m, where m ranges from 1 to n, and wherein the standard deviation in the amount of DNA-product fragment having a particular m value from the median amount of the DNA-product fragments having m values ranging from 1 to n is less than the corresponding standard deviation where the target DNA polymer were sequenced in the presence of $Mg^{++}$ but in the absence of $Mn^{++}$, with all other sequencing conditions being equivalent.

18. The method of claim 4 wherein $Mn^{++}$ is present in the reaction mixture at a concentration ranging from about 100 $\mu$M to about 3 mM.

19. The method of claim 4 wherein $Mn^{++}$ is present in the reaction mixture at a concentration ranging from about 625 $\mu$M to about 1250 $\mu$M.

20. The method of claim 4 wherein $Mn^{++}$ is present in the reaction mixture at a concentration ranging from about 0.9 mM to about 1.1 mM.

21. The method of claim 4 wherein $Mn^{++}$ is present in the reaction mixture at a concentration of about 1.0 mM.

22. A method for inhibiting pyrophosphorolysis during chain-termination DNA sequencing performed in a sequencing reaction mixture containing a nucleic acid primer, a nucleic acid template, deoxyribonucleotide triphosphates, a chain terminating agent, a DNA polymerase and $Mg^{++}$, the method comprising adding a $Mn^{++}$ to the sequencing reaction mixture in a concentration effective to inhibit pyrophosphorolysis.

23. The method of claim 22 wherein the $Mn^{++}$ is added to the sequencing reaction mixture at a time which is less than one hour before the DNA sequencing is performed.

24. The method of claim 22 wherein the DNA polymerase is a pol-I type D A/polymerase having polymerase activity toward dideoxyribonucleoside triphosphates which is at least about equal to its polymerase activity toward deoxyribonucleoside triphosphates.

* * * * *